United States Patent
Robinson (10) Patent No.: US 11,135,336 B2
(45) Date of Patent: Oct. 5, 2021

(54) THIN-FILM VEHICLES THAT STABILIZE HIGHLY REACTIVE ACTIVE INGREDIENTS

(71) Applicant: L'Oreal, Paris (FR)

(72) Inventor: Michael Robinson, Brooklyn, NY (US)

(73) Assignee: L'Oreal, Paris (FR)

( * ) Notice: Subject to any disclaimer, the term of this patent is extended or adjusted under 35 U.S.C. 154(b) by 110 days.

(21) Appl. No.: 16/587,591

(22) Filed: Sep. 30, 2019

(65) Prior Publication Data
US 2021/0093747 A1 Apr. 1, 2021

(51) Int. Cl.
| | |
|---|---|
| *A61L 15/28* | (2006.01) |
| *A61L 15/44* | (2006.01) |
| *A61L 31/14* | (2006.01) |
| *C08J 5/04* | (2006.01) |
| *C08J 5/24* | (2006.01) |
| *A61K 8/67* | (2006.01) |
| *A61K 8/73* | (2006.01) |
| *A61K 8/365* | (2006.01) |
| *A61K 8/02* | (2006.01) |
| *A61Q 19/00* | (2006.01) |

(52) U.S. Cl.
CPC .............. *A61L 15/28* (2013.01); *A61L 15/44* (2013.01); *A61L 31/145* (2013.01); *C08J 5/047* (2013.01); *C08J 5/24* (2013.01)

(58) Field of Classification Search
CPC ........ A61L 15/28; A61L 15/44; A61L 31/145; C08J 5/047; C08J 5/24; A61K 8/676; A61K 8/73; A61K 8/365; A61K 8/0212; A61Q 19/00
See application file for complete search history.

(56) References Cited

U.S. PATENT DOCUMENTS

| | | | |
|---|---|---|---|
| 4,220,152 A | 9/1980 | Dresback | |
| 5,409,703 A | 4/1995 | McAnalley et al. | |
| 5,423,736 A | 6/1995 | Cartmell et al. | |
| 5,731,365 A | 3/1998 | Engelhardt et al. | |
| 5,762,620 A | 6/1998 | Cartmell et al. | |

(Continued)

FOREIGN PATENT DOCUMENTS

| | | |
|---|---|---|
| EP | 0122771 A1 | 10/1981 |
| EP | 0355536 A2 | 2/1990 |

(Continued)

OTHER PUBLICATIONS

International Search Report and Written Opinion dated Feb. 25, 2021, issued in corresponding International Application No. PCT/US2020/052242, filed Sep. 23, 2020, 20 pages.

*Primary Examiner* — Trevor Love
(74) *Attorney, Agent, or Firm* — Christensen O'Connor Johnson Kindness, PLLC (57) ABSTRACT

A method of protecting an active ingredient before using as a skin treatment includes packaging the active ingredient in a water soluble polysaccharide. The package includes a substrate, comprising a first and second side configured to bring together the water soluble polysaccharide with the active ingredient and a hydrogel, wherein the first side includes the water soluble polysaccharide with the active ingredient on the exterior, and the second half includes the hydrogel on the exterior. Once brought into contact for a sufficient time to allow the polysaccharide to dissolve, at least the hydrogel layer with the infused active ingredient can be peeled from the substrate to use as a facial mask for treating the skin with the active ingredient.

10 Claims, 7 Drawing Sheets

(56) References Cited

U.S. PATENT DOCUMENTS

| | | | |
|---|---|---|---|
| 6,521,284 | B1 | 2/2003 | Parsons et al. |
| 6,855,743 | B1 | 2/2005 | Gvozdic |
| 7,678,716 | B2 | 3/2010 | Yahiaoui et al. |
| 8,066,117 | B2 | 11/2011 | Ueda et al. |
| 2008/0057811 | A1 | 3/2008 | Yahiaoui et al. |
| 2015/0267042 | A1 | 9/2015 | Munro et al. |
| 2018/0214354 | A1 | 8/2018 | Shin et al. |

FOREIGN PATENT DOCUMENTS

| | | |
|---|---|---|
| EP | 0976396 A1 | 2/2000 |
| JP | 2011102257 A | 5/2011 |
| KR | 101968631 B1 | 4/2019 |
| KR | 101977889 B1 | 5/2019 |
| WO | 2014007062 A1 | 9/2014 |
| WO | 2017144806 A1 | 8/2017 |

THIN-FILM VEHICLES THAT STABILIZE HIGHLY REACTIVE ACTIVE INGREDIENTS

SUMMARY

The present disclosure provides a formula and packaging that helps support thin film vehicles that stabilize highly reactive active ingredients, enables maximum stability of formulations, makes it easy for consumers to apply the product and deliver the highest concentration of active ingredients to the skin, and provides cost effective manufacturing solutions capable of being manufacture inline, effectively reducing costs.

In one embodiment, a package comprises a substrate having a first and second side, wherein the first side includes a water soluble polysaccharide with an active on the exterior, and the second half includes a hydrogel on the exterior, and the first and second sides are configured to be brought into contact with each other; and a facial mask including at least the hydrogel.

In one embodiment, the substrate is cardstock.

In one embodiment, a package further comprises a release liner juxtaposed on the second side and a barrier film layer juxtaposed between the release liner and hydrogel.

In one embodiment, the facial mask is releasably adhered to the release liner.

In one embodiment, the facial mask includes the hydrogel and barrier film layers.

In one embodiment, the polysaccharide is configured to dissolve in the hydrogel.

In one embodiment, the package includes an indicator to indicate when the polysaccharide is dissolved in the hydrogel.

In one embodiment, the indicator includes a halochromic compound.

In one embodiment, the mask has a fabiform or reniform shape.

In one embodiment, the hydrogel and water soluble polysaccharide are provided to be mirror shapes of each other.

In one embodiment, a method of protecting an active ingredient comprises providing the active ingredient in a water soluble polysaccharide; and providing a hydrogel in which the water soluble polysaccharide is dissolvable.

In one embodiment, the active ingredient is a skin treatment ingredient.

In one embodiment, the water soluble polysaccharide and hydrogel are provided on opposite sides of a substrate, and wherein the opposite sides of the substrate are configured to be brought into contact with each other.

In one embodiment, the substrate is a cardstock layer, and the hydrogel is juxtaposed on a barrier film, wherein the barrier film is juxtaposed on a release liner, wherein the release liner is juxtaposed on the cardstock layer.

In one embodiment, the water soluble polysaccharide with active ingredient and the hydrogel are provided in mirror shapes of each other on the substrate.

In one embodiment, at least the hydrogel is releasably attached to the substrate.

In one embodiment, a method of delivering an active ingredient to skin comprises bringing a water soluble polysaccharide with an active ingredient in contact with a hydrogel to dissolve the water soluble polysaccharide and infuse the active ingredient in the hydrogel; and bringing the hydrogel with infused active ingredient in contact with skin to be treated with the active ingredient.

In one embodiment, the method further comprises providing an indication when the water soluble polysaccharide with active ingredient has dissolved in the hydrogel.

In one embodiment, the method further comprises the water soluble polysaccharide with active ingredient and the hydrogel are provided on two sides of a foldable substrate.

In one embodiment, the method further comprises peeling the hydrogel with infused active ingredient from a substrate.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

It is known that high concentrations of certain active ingredients in cosmetic formulas are often sensitive to oxidative reactions that significantly degrade the active ingredient potency. Further, active ingredients can be combined with topical liquid formulas to provide a two-part solution that can be soaked onto masks that allow stability of the formula but are not easy to use and require additional cumbersome steps by the consumer. Often consumers have to manipulate very thin film substrates that break, cannot be applied evenly to the skin and fail to dissolve completely. Further, pre-wetted non-woven masks require complicated unfolding and may not fully dissolve the first-state film that is within skin contact. Lastly, these two-step solutions are not cost effective as they require multiple packaging formats and complex assembly.

The present disclosure relates to a package including a facial mask for delivery of an active ingredient. The active ingredient is initially in a dry state to prevent oxidation or other decomposition. In one embodiment, the package includes a semi-rigid backing substrate with a parting line allowing the otherwise semi-rigid backing substrate to be folded along the parting line to bring one side of the backing substrate over on top of the other side of the backing substrate. In one embodiment, a water-soluble polysaccharide thin film is imprinted on the semi-rigid backing substrate. The water-soluble polysaccharide thin film contains the active ingredient in a dry state to protect and stabilize the active ingredient before use.

To apply the active ingredient via use of a facial mask, the package also includes a complimentary hydrogel layer mirrored across the semi-rigid backing substrate parting line. The hydrogel layer is comprised in facial mask that may include the hydrogel layer and one or more layers. The facial mask is provided on the semi-rigid backing substrate. In one embodiment, the facial mask is defined by one or more layers, and in one embodiment, the facial mask can be peeled away from the semi-rigid backing substrate. The hydrogel layer being the exterior most layer of the facial mask further functions as an adhesive to adhere the peel-away facial mask to the skin surface. Therefore, when the two halves of the semi-rigid backing substrate are folded together, the dry polysaccharide film with the active ingredient dissolves into the top hydrogel layer of the facial mask, dissolving the polysaccharide substrate into the cross-linked hydrogel matrix and infusing the hydrogel with the active ingredient.

After a time period, the user opens the semi-rigid backing substrate, and then peels facial mask including the hydrogel layer with active ingredient from the semi-rigid backing substrate. Directly after removing the hydrogel layer with active ingredient from the backing substrate, the user can apply the mask to the skin using the hydrogel layer as an adhesive. Based on the skin's natural occlusivity and biomechanics of the formula and epidermis, the active ingredient within the hydrogel is made bioavailable.

In some embodiments, the facial masks and packages are made by combining one or more of the layers described below in a certain order. The layers can themselves be single ply or multi-ply. The layers comprising the mask can be glued, stitched or welded together, for example. Releasable adhesives can be used to adhere the facial mask onto a cover film or other layer from which the mask is peeled off and to adhere the mask to the skin.

Card Stock (100)

Cardstock layer 100 is a material that is used for its stiffness property and that can resist deformation. The cardstock layer 100 may be a single ply or multiple plys. Cardstock layer 100 can be made from bleached or unbleached pulp and paper products. Cardstock layer 100 can include corrugated layers in a sandwiched construction between two exterior layers. Cardstock layer 100 may also include webs of nonwoven fibers. The manner of spinning the fibers into a web can be one of several known spinning methods. Fibers can include natural and synthetic fibers. Natural fibers include, but are not limited to, cellulose or derivatives of cellulose.

Release Liner (200)

A release liner layer 200 is provided juxtaposed on the cardstock backing substrate 100. In one embodiment, the release liner 200 facilitates separation of the facial mask from the cardstock 100. In one embodiment, the release liner layer 200 is comprised of a synthetic polymer film. In one embodiment, the release liner 200 comprises a polyethylene film. In one embodiment, the release liner comprises a Kraft paper material. Other suitable synthetic polymers include, but are not limited to, polyvinylidene chloride, polyethylene polyproplyene, and the like.

In one embodiment, the thickness of the release liner 200 is from 0.001 to 0.010 inches. In one embodiment, the thickness of the release liner 200 is from 0.003 to 0.007 inches. In one embodiment, the thickness of the release liner 200 is about 0.005 inches.

Thin Film Barrier (300)

The barrier film layer 300 is for preventing the migration of air and or water or both air and water. In one embodiment, the barrier film layer 300 is one of the exterior most layers of the facial mask, the hydrogel layer being the other. Since the hydrogel layer will be applied on the skin, the barrier layer 300 will be on the exterior once the facial mask is adhered to the skin.

In one embodiment, the barrier film layer 200 comprises a metallized film (CELPLAST O2 sealant). In one embodiment, the barrier film layer 200 comprises a metallized low density polyethylene film. In one embodiment, the barrier film layer 200 comprises a metallized polypropylene film. In one embodiment, the barrier film layer 200 comprises a metallized polyethylene terephthalate film. In one embodiment, the barrier film layer 200 comprises a biaxially-oriented polypropylene film. In one embodiment, the barrier film layer 200 comprises a low density polyethylene film. In one embodiment, the barrier film layer 200 comprises a polyacryclic acid film.

In some embodiments, barrier film 200 is a single ply. In some embodiments, the barrier film 200 comprises multiple plys.

In one embodiment, the use of masks on the face requires that the films comprising the masks have a certain conformability, meaning the ability to conform to the contours of the face. Conformability is measured by a force given a certain extensibility or by a bending length over time value. The parameters are described in Example 2 and FIGS. 3, 4A, 4B, 4C, and 4D. In one embodiment, the barrier film 200 layer has conformability measured by an extensibility of 20% at a force of less than 70,000 lbs or less than 10,000 lbs or less than 25,000 lbs, or a bending length over time value of 3 mm to 65 mm at 10 mins.

In one embodiment, the thickness of the barrier film layer 200 is from 0.0001 to 0.010 inches. In one embodiment, the thickness of the barrier film layer 200 is from 0.0005 to 0.007 inches. In one embodiment, the thickness of the barrier film layer 200 is about 0.0015 inches.

Hydrogel Layer (400)

As used herein, "hydrogel" of the hydrogel layer 400 refers to a substance formed when an organic hydrophilic polymer, (natural or synthetic) that is crosslinked via covalent, ionic, or hydrogen bonds to form a three-dimensional open-lattice network structure that entraps water molecules to form a gel.

Examples of hydrogel polymers, also referred to as water "superabsorbent polymers" include, but are not limited to: polymers resulting from polymerization with partial cross-linking of water-soluble ethylenically unsaturated monomers, such as acrylic or vinylic polymers, and such polymers would include crosslinked and neutralized polyacrylates; starch-grafted polyacrylates; acrylamide/acrylic acid copolymers, including sodium salts of such polymers; starch-grafted acrylamide/acrylic acid, including sodium and potassium salts of such polymers; isobutylene/maleic anhydride copolymers; sodium and potassium salts of carboxymethylcellulose; crosslinked salts of polyaspartic acid; and chitosan/polyvinylpyrrolidone and chitosan/polyethyleneimine combinations.

In some embodiments, hydrogels contains 90% or more water (e.g., 80% or more, 70% or more, 60% or more, or 50% or more) by volume. The hydrogel layer 400 can include a releasable adhesive to attach the hydrogel layer 400 directly to the skin.

A characteristic of the hydrogel layer 400 is the peel strength. Representative peel strengths are given in Table 1 of Example 1. Peel strength of the hydrogel layer 400 can range from 0.4 to 25 N/inch or any value in between this lower and upper limit.

In one embodiment, the thickness of the hydrogel layer 400 is from 0.025 to 0.045 inches. In one embodiment, the thickness of the hydrogel layer 400 is from 0.030 to 0.040 inches. In one embodiment, the thickness of the hydrogel layer 400 is about 0.035 inches.

Actives Dissolving Layer (500)

Active ingredients or actives in this disclosure include any one or more compounds and compositions that are applied to skin or that transfer through the skin to provide a user with a treatment. Actives include, but are not limited to, medicines, pharmaceuticals, nutraceuticals, cosmetics, micronutrients, vitamins, minerals, and the like. In one embodiment, the active is ascorbic acid (vitamin C) or any derivative thereof. In one embodiment, the active is salicylic acid.

Actives are provided on or within the dissolving layer 500. The dissolving layer 500 protects or stabilizes the active ingredient prior to using. In one embodiment, the dissolving layer 500 includes a water soluble polysaccharide polymer. In one embodiment, the water soluble polysaccharide polymers are fibers, and the dissolving layer 500 is a non-woven material fabric.

Dissolving polysaccharide polymers are disclosed in US 2015/0374098. The term "polysaccharide" includes any polymer having several saccharides (or monosaccharides) having the general formula:

—[$C_x(H_2O_y)$]$_n$— (in which y is generally x−1)

and linked together via O-oside bonds.

The water-soluble polysaccharides that may be used in the present disclosure are especially chosen from starches, gellans, scleroglucan gum, guar gum, konjac, agar, and celluloses such as hydroxyethylcellulose and hydroxypropylcellulose, and mixtures thereof. Starches are preferentially used.

The term "water-soluble" means partially or totally soluble in water to give a gelled or thickened solution at a concentration of 1% active material in water. The starches that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the botanical origin of the starches. The amylose/amylopectin weight ratio may range from 30/70 (corn) to 16/84 (rice). The molecular weight of the amylose is preferably up to 1 million by weight and that of the amylopectin is preferably from 100 to 500 million by weight.

The starch molecules used in the present invention may be unmodified or chemically or physically modified.

Their botanical origin may be cereals or tubers. Thus, the natural starches may be chosen from corn starch, rice starch, tapioca starch, cassava starch, barley starch, potato starch, wheat starch, sorghum starch, palm starch and pea starch.

Among the unmodified starches, mention may be made of unmodified corn starches (INCI name: *Zea mays* starch), for instance the products sold under the trade name Farmal CS®, in particular the commercial product Farmal CS 3650® from the company Corn Products International.

Mention may also be made of unmodified rice starches (INCI name: *Oryza sativa* (rice) starch), for instance the commercial product Remy DR I® sold by the company Beneo-Remy.

Starches used are modified by crosslinking with functional agents capable of reacting with the hydroxyl groups of the starch molecules, which will thus bond together (for example with glyceryl and/or phosphate groups).

Monostarch phosphates (of the type St-O—PO—(OX)$_2$), distarch phosphates (of the type St-O—PO—(OX)—O-St) or even tristarch phosphates (of the type St-O—PO—(O-St)$_2$) or mixtures thereof may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Use will preferentially be made of distarch phosphates or of compounds rich in distarch phosphate, in particular the distarch phosphate hydroxypropyl ethers having the INCI name: Hydroxypropyl Starch Phosphate, for instance the products sold under the trade names Farinex VA70 C or FARMAL MS 689® from the company Avebe Stadex; the products sold under the trade names Structure BTC®, Structure HVS®, Structure XL® or Structure Zea® from National Starch (corn distarch phosphate).

Preferentially, the starch will be chosen from unmodified corn starches, unmodified rice starches and corn distarch phosphates, or mixtures thereof.

Figure 1:
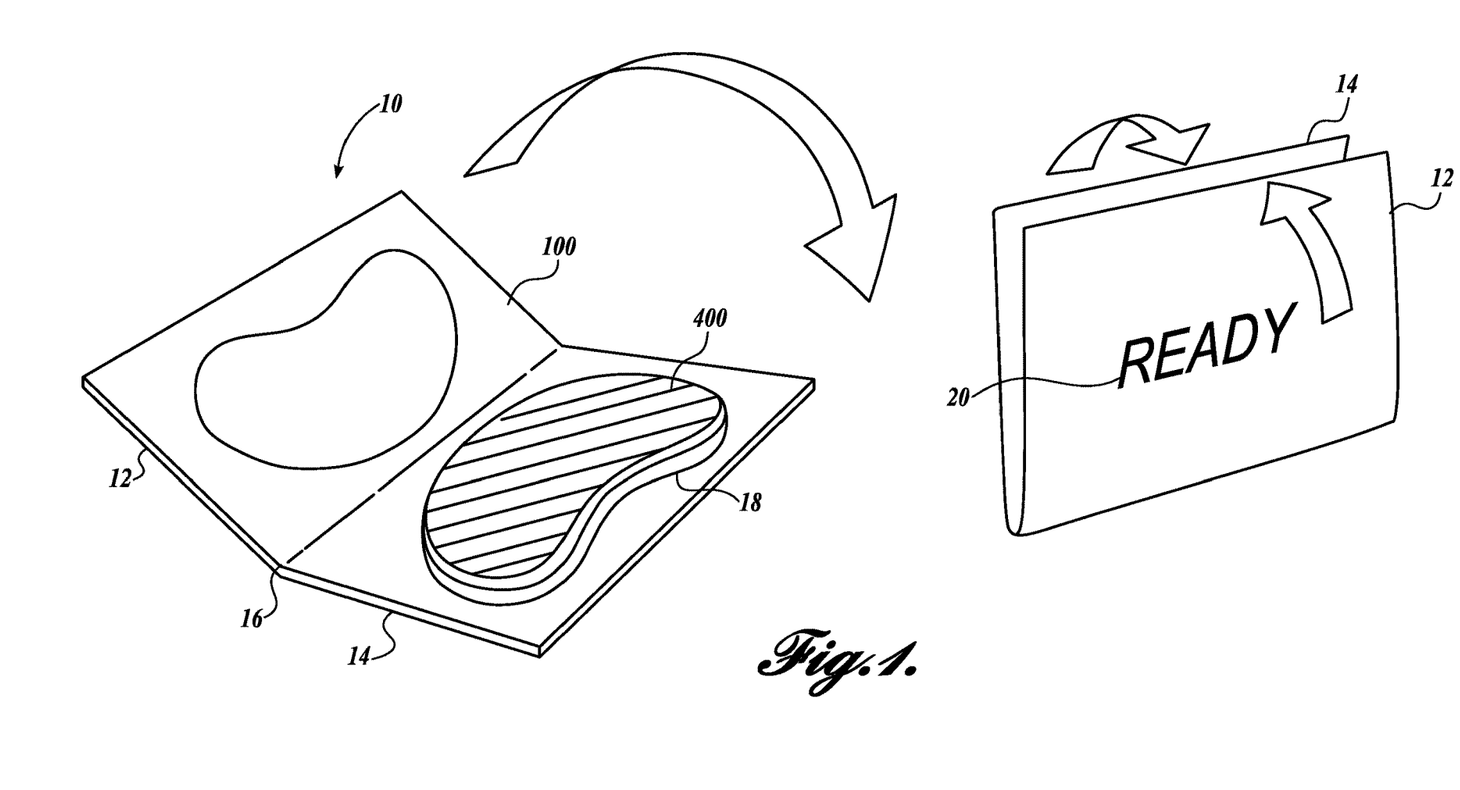
FIG. 1 is a package for a facial mask with an active ingredient.
Figure 2:
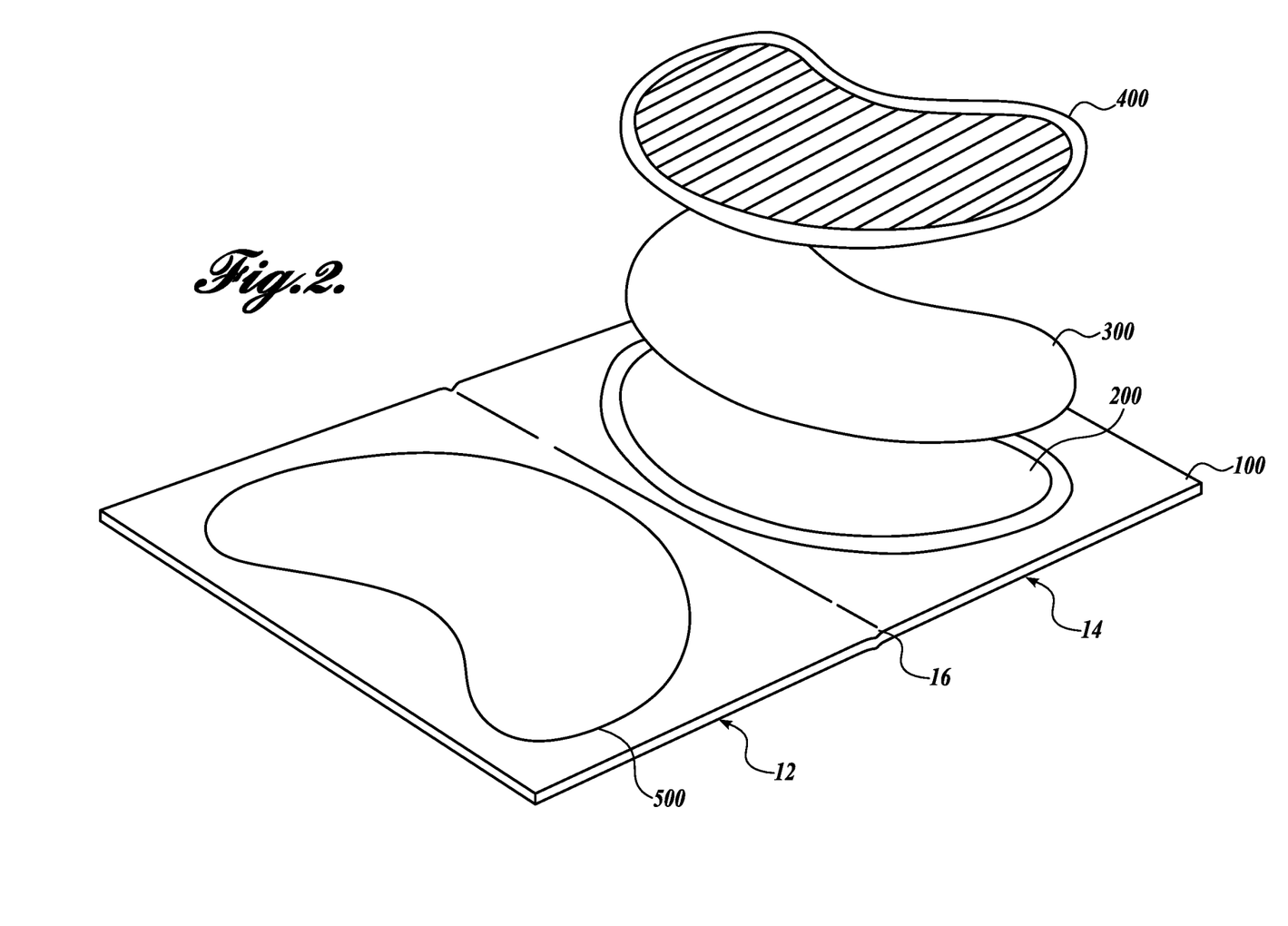
FIG. 2 is the package of FIG. 1 showing the component layers.
Figure 3:
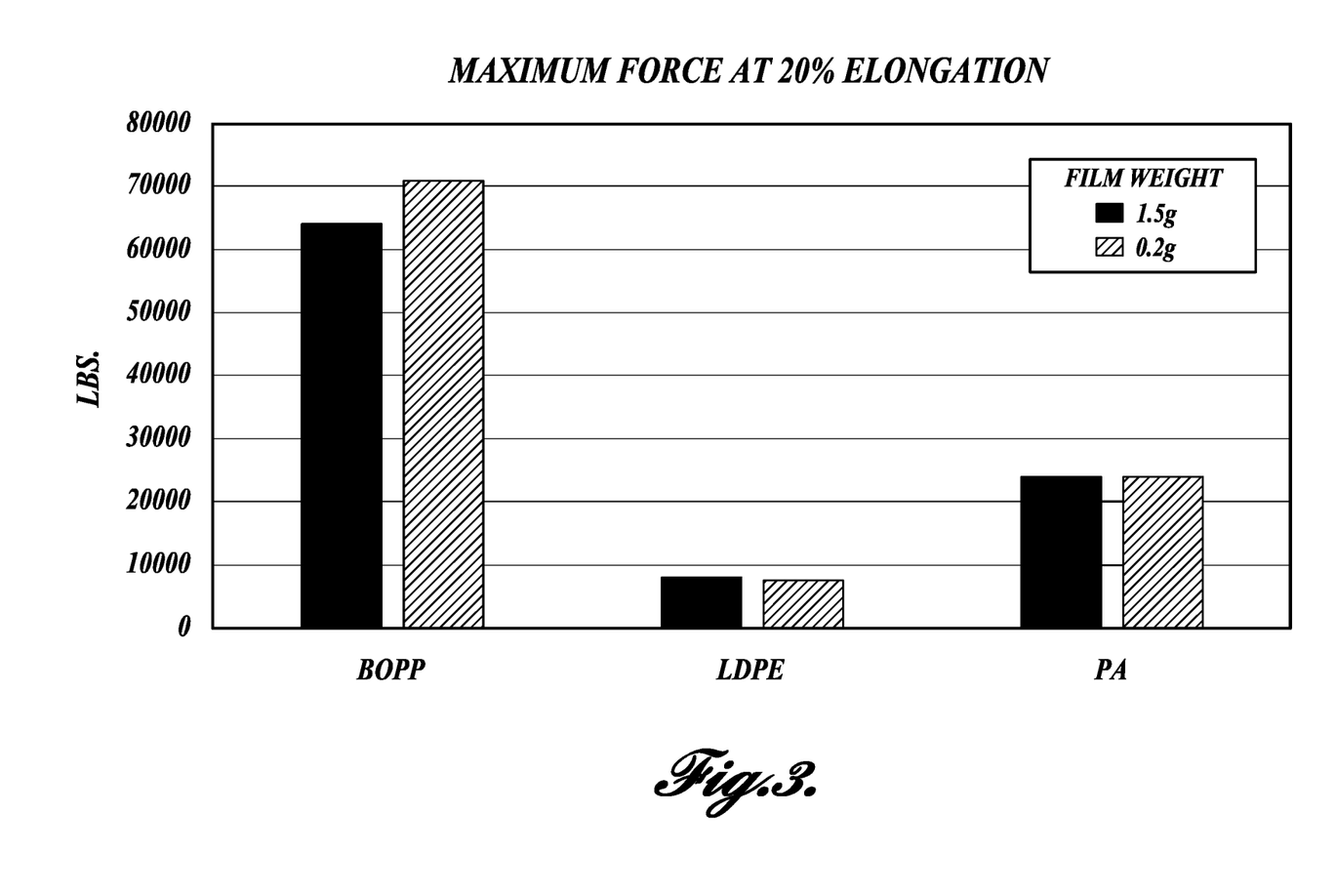
FIG. 3 is a bar graph comparing the bending force of various films at two different weights.
Figure 4A:
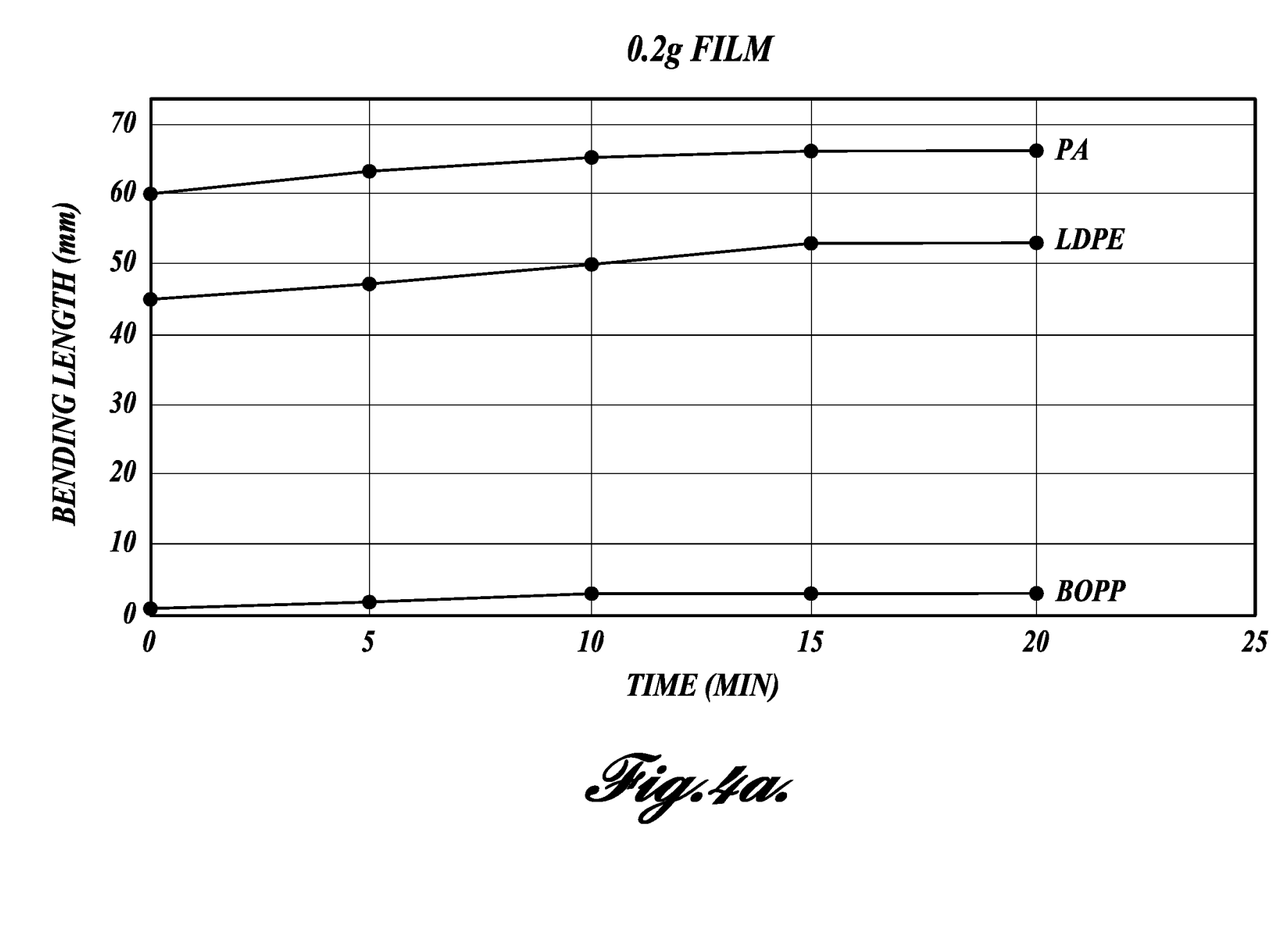
FIG. 4A is a graph of the bending length over time of various films at a weight of 0.2 g/si (square inches)
Figure 4B:
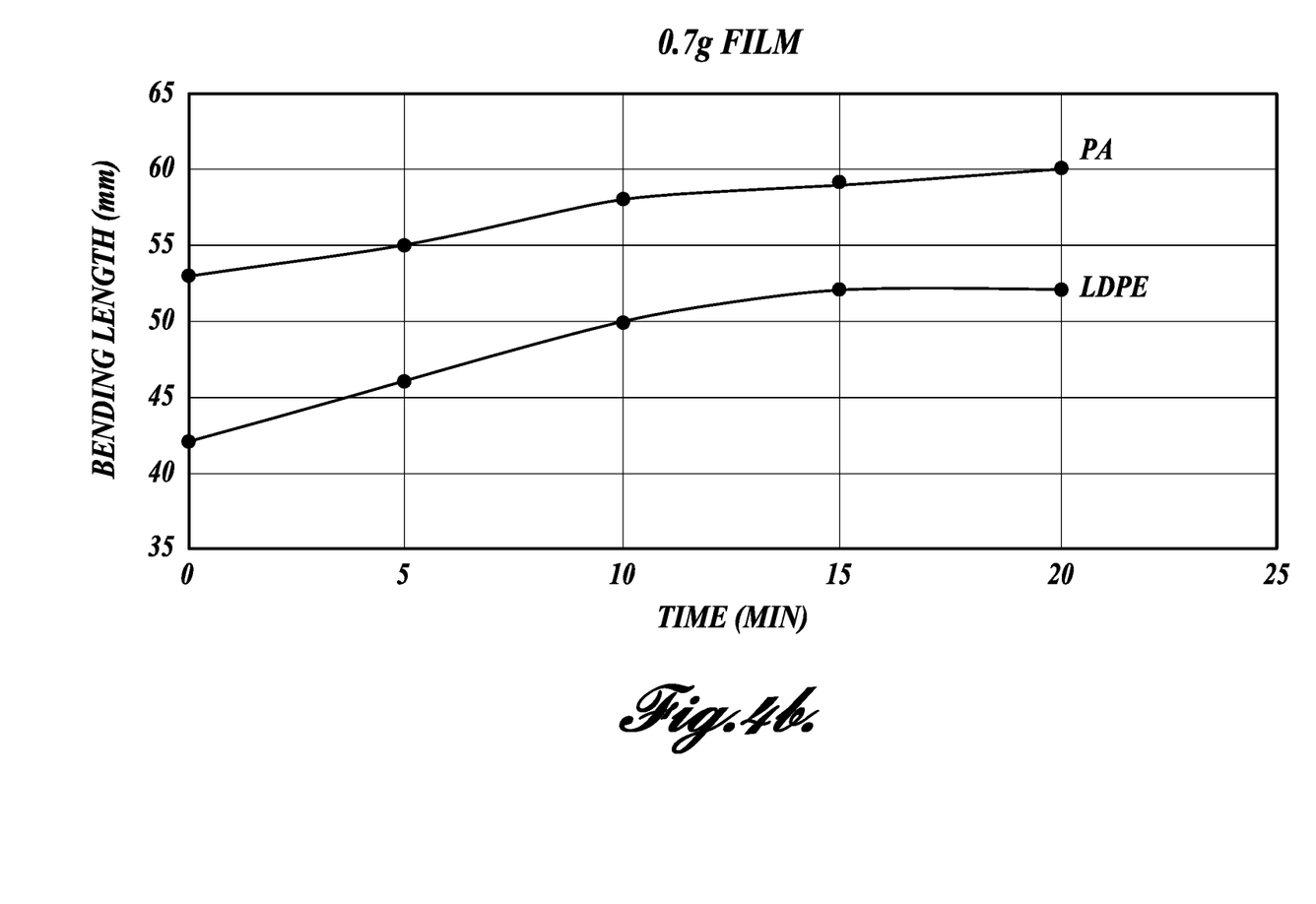
FIG. 4B is a graph of the bending length over time of various films at a weight of 0.7 g/si.
Figure 4C:
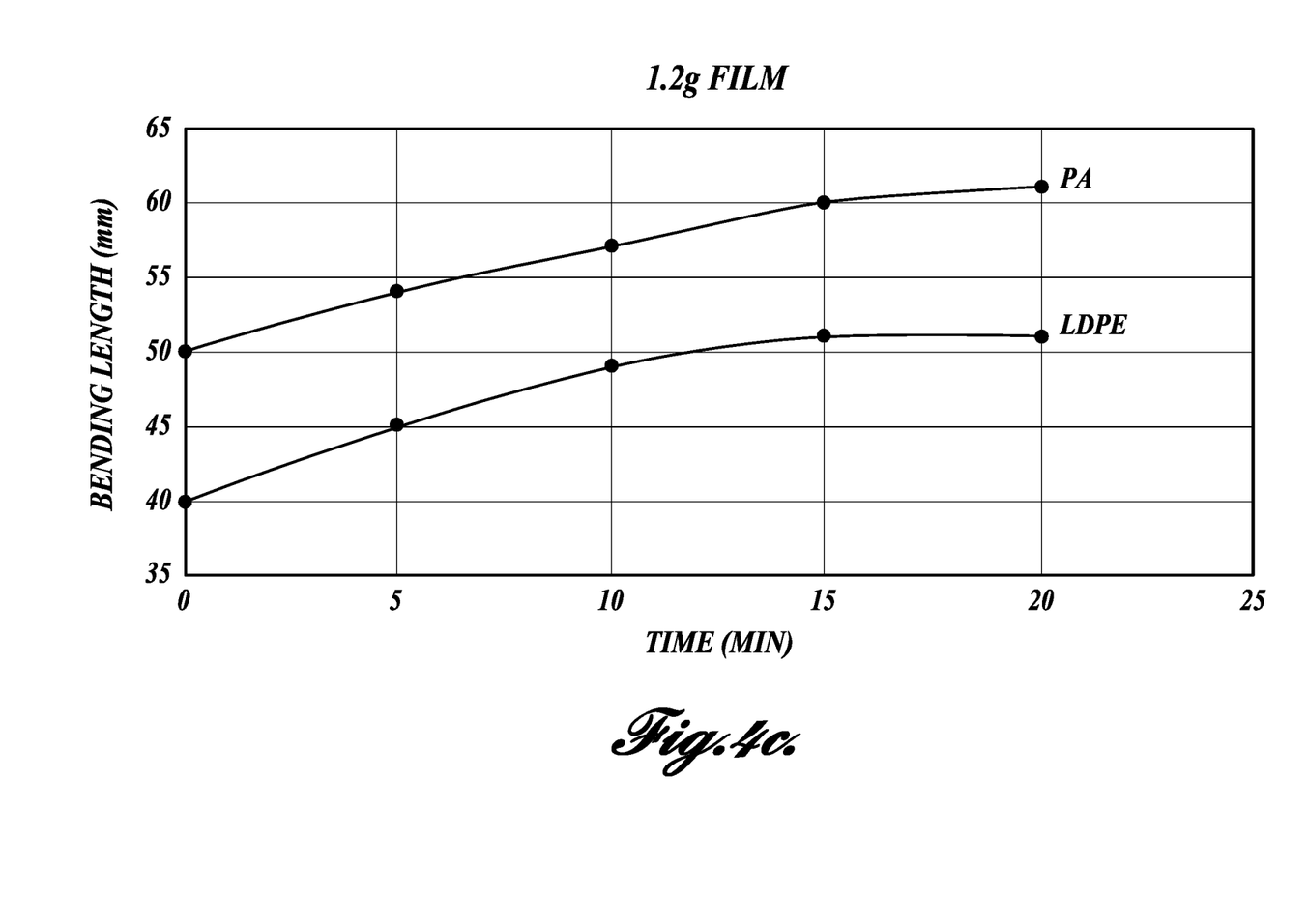
FIG. 4C is a graph of the bending length over time of various films at a weight of 1.2 g/si.
Figure 4D:
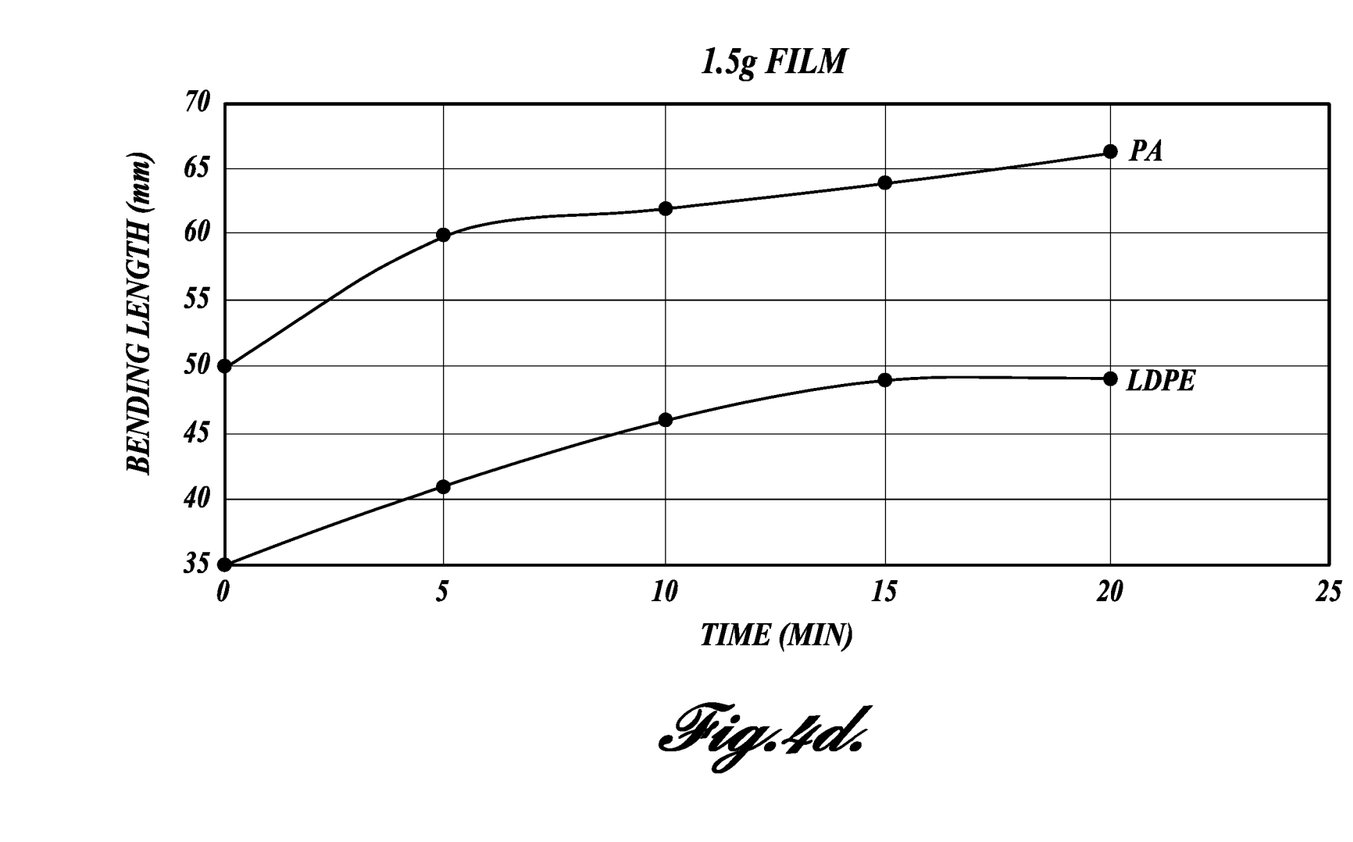
FIG. 4D is a graph of the bending length over time of various films at a weight of 1.5 g/si.

Referring to FIGS. 1 and 2, a representative packaging vehicle (package) in the form of a card 10 is illustrated. In one embodiment, the card 10 includes a single mask. The card 10 is generally a rectangle shape with a parting line or crease 16 approximately at the middle to allow the card 10 to fold at the crease 16 and to provide a first side 12 and second side 14.

Referring to FIG. 2, in one embodiment, the card 10 is comprised of the following layers in the following order. The cardstock layer 100 forms both halves 12, 14 of the card 10 and is used as the semi-rigid backing substrate onto which other layers are placed. The release liner layer 200 is juxtaposed above the cardstock layer 100 on the card half 14. However, the release liner layer 200 can extend into the second half 12. The release liner layer 200 is not part of the facial mask, and when the facial mask is peeled off, the release liner layer 200 can remain on the cardstock layer 100. The barrier film layer 300 is juxtaposed above the release liner layer 200. The hydrogel layer 400 is juxtaposed above the barrier film layer 300. In one embodiment, the layers 300 and 400 which are intended to remain as a unit, are provided in the shape of the mask that is placed on the skin.

The dissolving layer 500 with the active ingredient made from the dissolving polysaccharide is juxtaposed on the cardstock layer 100 on the card half 12. The release liner layer 200 can extend into the second half 12, in which case, the dissolving layer 500 will be juxtaposed on the release liner 200. In one embodiment, the shape of the actives dissolving layer 500 is coextensive with and mirrors the shape of the hydrogel layer 400, such that when the halves 12, 14 are brought together by folding along the crease 16, the dissolving layer 500 is brought into contact with the hydrogel layer 400. The shape of dissolving layer 500 and the hydrogel layer 400 can generally be a fabiform or reniform shape.

Referring to FIG. 1, when the halves 12, 14 of the card 10 are brought together by folding, the actives dissolving layer 500 contacts the hydrogel layer 400 which causes the actives dissolving layer 500 to dissolve into the hydrogel layer 400, thereby infusing the hydrogel layer 400 with the active or actives. After a sufficient period of time, the card 10 is reopened, and the mask having layers 300 and 400 is removed from the card 10 along the pre-scored line 18. In one embodiment, the barrier film layer 300 is provided over the entire card half 14, and is scored to peel off in the shape of the facial mask. In such case, the hydrogel layer 400 is provided in the shape of the facial mask juxtaposed next to the barrier film layer 300. Thus, the hydrogel layer 400 is not scored since it is already shaped, and is juxtaposed within the part of the barrier film layer 300 that is scored and can be peeled off. In one embodiment, both the barrier film layer 300 and the hydrogel layer 400 are provided and juxtaposed already in the shape of the mask onto the release liner layer 200, so no scoring is necessary of either layer 300 or 400. In still another embodiment, both the barrier film layer 300 and the hydrogel layer 400 cover all or nearly all the surface area of the second side 14, so both layers 300 and 400 would require scoring to allow peeling off of the facial mask.

The mask includes at least the hydrogel layer 400. The mask that is placed on the skin generally has a fabiform or reniform (kidney or bean) shape with two lobes extending out from the middle at an obtuse angle, for example. However, masks can come in other shapes.

In one embodiment, the card 10 provides a visual indication to the consumer when the actives dissolving layer 500 has fully dissolved into the hydrogel layer 400 via a visual indicator, such as letters 20 spelling READY. The visual indication 20 can be indicated by a change in state or color. In one embodiment, the visual indicator 20 may be rendered based on halochromic compounds added in small amounts to the hydrogel 400, polysaccharide 300, or the cardstock 100 layers. In one embodiment, the visual indicator 20 may be dependent on ph. Ph sensitive compounds, such as phenolphthalein, methyl red, and bromothymol blue can be added in small amounts to the hydrogel 400, polysaccharide 300, or tie layer.

EXAMPLES

1. Example Demonstrating Peel Strength of Hydrogel Layer

TABLE 1

Peel strength of various skin adhesive layers

| # Sample | Peel test 1 (N/Inch) | Peel test 2 (N/Inch) |
|---|---|---|
| 193B-65.7 | 22 | 25 |
| 193E-37 | 6 | 6.5 |
| 193G-35.9 | 4.8 | 4 |
| 193I-37.6 | 6.5 | 5.5 |
| 193F-67.3 | 10 | 8.4 |
| 193H-65.4 | 6.4 | 6 |
| 193J-67.2 | 8 | 8.8 |
| 193A-36.1 (The coating wasn't even on the surface) | 9 | 8 |
| 193C-35.5 | 8 | 8.7 |
| 193D-66.4 | 11.5 | 12.5 |
| 92892-Silicone | 16.2 | 16.5 |
| 93257-PU | 3 | 2.5 |
| 93276-nonwoven | 3.5 | 3 |
| AG625-Sensing Gel | 4 | 4 |
| AG735-Sensing Gel | 1 | 0.7 |
| AG548-Sensing Gel | 0.4 | 0.5 |

2. Example Demonstrating Film Conformability

Conformability experiments involved three different films of biaxially-oriented polypropylene (BOPP), low density polyethylene (PE), of polyacrylic acid (PA) at four different weights (0.2, 0.7, 1.2 and 1.5 g/si). The conformability of the package was measured by two prevalent methods used in health care which is used to estimate the conformability of wound care laminates. In one embodiment, conformability is measured according to EN 13726-4. In this method, the dressings are sectioned into 25 mm widths and marks made on the sample 100 mm apart (L1). The samples are then positioned within a tensometer then extended 20% and the maximum load recorded, so that the extensibility can be calculated (lb or N/cm). The sample is held at this extension for 1 min, then, removed from the tensometer. The 2 marks on the sample are then re-measured (L2) and the percentage of the permanent set is calculated.

The maximum force measured in 20% elongation of the pouch made with the highest (1.5 g/si) and the lowest (0.2 g/si) coat weights in three different packaging films demonstrate the flexibility is driven by the film. See FIG. 3.

The second test method correlates the bending length of a laminate to its conformability to curved surfaces of a patient body where a higher bending length corresponds to a more conformable laminate. See FIGS. 4A, 4B, 4C, and 4D.

A comparison of the bending of the samples at 10 minutes shows the packaging film has the larger effect on conformability of the laminate from the following Table.

TABLE 2

| Bending Length (mm) of Packs at 10 min | | | | |
|---|---|---|---|---|
| | 0.2 g/si | 0.7 g/si | 1.2 g/si | 1.5 g/si |
| BOPP | 3 | 3 | 4 | 4 |
| PE | 50 | 50 | 49 | 46 |
| PA | 65 | 58 | 57 | 62 |

While illustrative embodiments have been illustrated and described, it will be appreciated that various changes can be made therein without departing from the spirit and scope of the invention.

The embodiments of the invention in which an exclusive property or privilege is claimed are defined as follows:

1. A package, comprising:
a substrate having a first and second side, wherein the first side includes a water soluble polysaccharide with an active on the exterior, and the second side includes a facial mask including at least a hydrogel on the exterior, and the first and second sides are configured to be brought into contact with each other.

2. The package of claim 1, wherein the substrate is cardstock.

3. The package of claim 1, further comprising a release liner juxtaposed on the second side and a barrier film layer juxtaposed between the release liner and hydrogel.

4. The package of claim 3, wherein the facial mask is releasably adhered to the release liner.

5. The package of claim 3, wherein the facial mask includes the hydrogel and barrier film layers.

6. The package of claim 1, wherein the polysaccharide is configured to dissolve in the hydrogel.

7. The package of claim 1, wherein the package includes an indicator to indicate when the polysaccharide is dissolved in the hydrogel.

8. The package of claim 7, wherein the indicator includes a halochromic compound.

9. The package of claim 1, wherein the mask has a fabiform or reniform shape.

10. The package of claim 1, wherein the hydrogel and water soluble polysaccharide are provided to be mirror shapes of each other.

* * * * *